US005574132A

United States Patent [19]
Lacroix

[11] Patent Number: 5,574,132
[45] Date of Patent: Nov. 12, 1996

[54] PEPTIDES AND MIXTURES THEREOF FOR DETECTING ANTIBODIES TO HEPATITIS C VIRUS (HCV)

[75] Inventor: Martial Lacroix, Brossard, Canada

[73] Assignee: BioChem Immunosystems Inc., Quebec, Canada

[21] Appl. No.: 681,701

[22] Filed: Apr. 5, 1991

[51] Int. Cl.$^6$ ............................... C07K 7/02; C07K 7/08; C07K 14/18

[52] U.S. Cl. .................... 530/323; 530/324; 530/325; 530/326; 530/327; 530/332; 930/30; 930/220

[58] Field of Search ........................... 435/5, 7.92, 7.1; 530/326, 324, 323, 325, 327; 514/12, 13, 14

[56] References Cited

U.S. PATENT DOCUMENTS

5,106,726  4/1992  Wang .......................... 435/5

FOREIGN PATENT DOCUMENTS

| | | | |
|---|---|---|---|
| 0293274 | 11/1988 | European Pat. Off. | ......... C12N 15/00 |
| 0363025 | 4/1990 | European Pat. Off. | . |
| 0377303 | 7/1990 | European Pat. Off. | ......... C12N 15/51 |
| 0388232 | 9/1990 | European Pat. Off. | . |
| 0414475 | 2/1991 | European Pat. Off. | . |
| 0416725 | 3/1991 | European Pat. Off. | . |
| 0419182 | 3/1991 | European Pat. Off. | . |
| 0435229 | 7/1991 | European Pat. Off. | ......... C07K 15/00 |
| 0442394 | 8/1991 | European Pat. Off. | .......... C07K 7/08 |
| 0445801 | 9/1991 | European Pat. Off. | .......... C07K 7/04 |
| 0445423 | 9/1991 | European Pat. Off. | ..... G01N 33/576 |
| 0450931 | 10/1991 | European Pat. Off. | ..... G01N 33/576 |
| 0471356 | 2/1992 | European Pat. Off. | .......... C07K 7/08 |
| 0484787 | 5/1992 | European Pat. Off. | .......... C07K 7/08 |
| 2212511 | 7/1989 | United Kingdom | ............ C12N 7/00 |
| WO82/00205 | 1/1982 | WIPO | ............................ G01N 33/54 |
| WO89/04669 | 6/1989 | WIPO | ............................ A61K 39/12 |
| WO90/14436 | 11/1990 | WIPO | ................................ C12Q 1/20 |

OTHER PUBLICATIONS

Tabler et al., "Evaluation of Indeterminate C22–3 Reactivity in Volunteer Blood Donors", Transfusion, vol. 34, No. 2, pp. 130–134, 1994.

T. Arima et al., "Cloning of a cDNA Associated with Acute and Chronic Hepatitis C Infection Generated from Patient's Serum RNA", Chemical Abstracts, vol. 112, No. 3, p. 209, abstract 1980n (1990).

G. Kuo et al., "An Assay for Circulating Antibodies to a Major Etiologic Virus of Human Non–A, Non–B Hepatitis", Science, 244, pp. 362–364 (1989).

M. Moriayama et al., "Detection of Serum HCV Antibody by ELISA Using the C100 Synthetic Peptide", Chemical Abstracts, vol. 115, No. 3, p. 587, abstract 27240h (1991).

S. Nakanishi et al., "Antigenic Peptide of a Non–A Non–B Hepatitis Virus Antigen", Chemical Abstracts, vol. 112, No. 9, p. 436, abstract No. 73383t (1990).

H. Okamoto et al., "Enzyme–linked Immunosorbent Assay for Antibodies Against the Capsid Protein of Hepatitis C Virus with a Synthetic Oligopeptide", Jpn. Exp. Med., 60(4), pp. 223–233 (1990).

K. Takeuchi et al., "Nucleotide Sequence of Core and Envelope Genes of the Hepatitis C Virus Genome Derived Directly from Human Healthy Carriers", Nucl. Acid Res., 18(5), p. 426 (1990).

T. Arima et al., "A cDNA Clone Encoding a Peptide Highly Specific for Hepatitis C Infection", Gastroenterologia Japonica, 25, pp. 218–222 (1990).

G. J. Dawson et al., "Detection of Antibodies to Hepatitis C Virus in U.S. Blood Donors", Journal of Clinical Microbiology, 29, pp. 551–556 (1991).

B. Hosein et al., "Improved Serodiagnosis of Hepatitis C Virus Infection with Synthetic Peptide Antigen from Capsid Protein", Proc. Natl. Acad. Sci. USA, 88, pp. 3647–3451 (1991).

N. Kato et al., "A Structural Protein Encoded by the 5' Region of the Hepatitis C Virus Genome Efficiently Detects Viral Infection", Jpn. J. Cancer Res., 81, pp. 1092–1094 (1990).

K. Muraiso et al., "Structural Protein of Hepatitis C Virus Expressed In E. Coli Facilitates Accurate Detection of Hepatitis C Virus", Biochem. Biophys. Res. Commun., 172, pp. 511–516 (1990).

C. L. van der Poel et al., "Confirmation of Hepatitis C Virus Infection by New Four–Antigen Recombinant Immunoblot Assay", Lancet, 337, pp. 317–319 (1991).

Primary Examiner—David Guzo
Attorney, Agent, or Firm—Nixon & Vanderhye

[57] ABSTRACT

This invention relates to novel peptides and mixtures thereof useful for detecting HCV infections. These peptides are also useful as active ingredients in vaccines against HCV infection.

7 Claims, 3 Drawing Sheets

Fig. 1

Amino acid sequence of the putative core gene product of HCV (SEQ ID NO: 16).

1
|
MSTNPKPQRKTKRNTNRRPQDVKFPGGGQIVGGVYLLPRRGPRLGVRATR

KTSERSQPRGRRQPIPKARRPEGRTWAQPGYPWPLYGNEGLGWAGWLLSP

RGSRPSWGPNDPRRRSRNLGKVIDTLTCGFADLMGYIPLVGAPLGGAARA

190
                                        |
LAHGVRVLEDGVNYATGNLPGCSFSIFLLALLSCLTIPAS

Fig. 2

Amino acid sequence of the putative envelope gene product of HCV (SEQ ID NO: 17).

191
|
AYEVRNVSGIYHVTNDCSNSSIVYEAADVIMHAPGCVPCVRENNSSRCWV

ALTPTLAARNASVPTTTLRRHVDLLVGTAAFCSAMYVGDLCGSVFLISQL

FTFSPRRHETVQDCNCSIYPGHVSGHRMAWDMMMNWSPTAALVVSQLLRIP

380
                        |
QAVMDMVAGAHWGVLAGLAYYSMVGNWAKVLIVMLLFAG

Fig. 3

```
                              1                        26
                              |                         |
(SEQ ID NO: 1)     -MSTNPKPQRKTKRNTNRRPQDVKFPG-              (BCH-423)

191          208
                             |            |
(SEQ ID NO: 2)     -AYEVRNVSGIYHVTNDSS-                      (BCH 427)

222                243
                            |                  |
(SEQ ID NO: 3)     -HAPGSVPSVRENNSSRCWVALT-                  (BCH 429)

282                303
                            |                  |
(SEQ ID NO: 4)     -GSVFLISQLFTFSPRRHETVQD-                  (BCH 430)

19        31
                             |         |
(SEQ ID NO: 5)     -PQDVKFPGGGQIV-                           (BCH-436)

12               31
                             |                |
(SEQ ID NO: 6)     -KRNTNRRPQDVKFPGGGQIV-                    (BCH-437)

6                        31
                             |                         |
(SEQ ID NO: 7)     -KPQRKTKRNTNRRPQDVKFPGGGQIV-              (BCH-438)

1                              31
                             |                               |
(SEQ ID NO: 8)     -MSTNPKPQRKTKRNTNRRPQDVKFPGGGQIV-         (BCH-439)

256                          284
                             |                            |
(SEQ ID NO: 9)     -TTLRRIIVDLLVGTAAFCSAMYVGDLCGSV           (BCH 440)

101                       127
                             |                         |
(SEQ ID NO: 10)    -RGSRPSWGPNDPRRRSRNLGKVIDTLT-             (BCH-443)

23                  46
                              |                   |
(SEQ ID NO: 11)    -KFPGGGQIVGGVYLLPRRGPRLGV-                (BCH-446)

59               81
                              |                |
(SEQ ID NO: 12)    -RGRRQPIPKARRPEGRTWAQPGY-                 (BCH-448)

210                231
                             |                  |
(SEQ ID NO: 13)    -SSIVYEAADVIMHAPGSVPSVR-                  (BCII-458)

41                        65
                              |                         |
(SEQ ID NO: 14)    -GPRLGVRATRKTSERSQPRGRRQPI-               (BCII-461)

329                   351
                             |                     |
(SEQ ID NO: 15)    -TAALVVSQLLRIPQAVMDMVAGA-                 (BCH 464)
```

PEPTIDES AND MIXTURES THEREOF FOR DETECTING ANTIBODIES TO HEPATITIS C VIRUS (HCV)

TECHNICAL FIELD OF THE INVENTION

This invention relates to novel linear peptides and mixtures thereof useful for detecting and quantifying HCV infections. These peptides are also useful as active ingredients in vaccines against HCV infections.

BACKGROUND OF THE INVENTION

In 1973, a new terminology, non-A, non-B hepatitis (NANB), was introduced to describe a form of hepatitis which was not associated with either the hepatitis A or the hepatitis B viruses. NANB was presumed to be caused by more than one agent. Indeed, two new viruses responsible for the transmission of hepatitis have since been identified. The first one, hepatitis E virus, is transmitted by contaminated water as is the hepatitis A virus. The second one, hepatitis C virus (HCV), similar to the hepatitis B virus, is transmitted mainly through infected blood. Hepatitis C is by far the most common form of viral hepatitis encountered in patients who are seronegative for hepatitis A and B.

Transfusion-associated hepatitis continues to be reported despite massive efforts to identify and eliminate all hepatitis virus infected blood donations. Asymptomatic carriers are common and they frequently progress towards cirrhosis and hepatocellular carcinoma within 10 to 30 years after infection. Depending on the country where it is found, HCV infections account for 50% to 90% of all post-transfusion hepatitis cases and indeed HCV poses a major public health problem worldwide.

Until recently, attempts to identify and isolate HCV were unsuccessful. Two American studies demonstrated that NANB infected sera were often found to have elevated alanine aminotransferase (ALT) activity or were positive for core antigen antibody of the hepatitis B virus (anti-HBc). Accordingly, in 1987, it was decided to screen all blood donations for both ALT and anti-HBc. These tests are believed to have prevented as much as 50% of transfusion-associated NANB hepatitis.

In 1989, HCV was identified and cloned (Choo et al. Science, 244, 349–362, 1989). HCV, a single stranded RNA virus of 10 kb, is a distant relative of the flaviviruses. The sequence of HCV RNA and comparison of that RNA to flavivirus RNA has permitted a general organization of HCV to be proposed. HCV RNA is believed to be read into a single precursor protein which is cleaved into 7 or 8 smaller protein fragments. The first zone of the precursor is believed to include three structural protein molecules called C (core), M (membrane) and E (envelope). However, the M and E proteins might be fused in a single protein. The second zone of the precursor includes five non-structural proteins named $NS_1$ to $NS_5$. $NS_2$ is presumably a protease and $NS_5$ is probably the RNA polymerase.

Several diagnostic tests for HCV using regions of the HCV viral proteins have been developed (e.g., Kuo et al. Science, 244, 362–364, 1989). One such test uses a protein fragment designated C100-3. It is a fused-protein containing the $NS_3$ and $NS_4$ non-structural proteins. In an ELISA this protein has not been shown to be 100% effective. For example, various reports indicate that the test detects only 10%–29% of the clinically diagnosed acute cases of HCV less than 90 days after infection, and only between 67% and 85% of the clinically diagnosed cases of chronic HCV (*HCV Learning Guide;* Abbott Diagnostics Educational Services, April 1990; Kuo et al. Science, 244, 362–364, 1989; Esteban et al. Lancet 2, 294–296, 1989; van der Poel et al. Lancet 2, 297–298, 1989; Janot et al. Lancet 2, 796–797, 1989; Bruix et al. Lancet 2, 1004–1006, 1989; Colombo et al. Lancet 2, 1006–1008, 1989). Thus, these assays do not display sufficient sensitivity to be useful in a HCV screening program.

The specificity of these HCV assays is also unacceptably low. Some false positive have been attributed to reactions with superoxide dismutase (the HCV C100-3 protein fragment used in the assay is expressed as a fusion protein with superoxide dismutase, SOD) (Ikeda et al. Lancet, 335:1345–6, 1990), to reactions to a rheumatoid factor (Theilman et al. Lancet, 335, 1346, 1990) or to a state of hyperglobulinemia, which is typically associated with autoimmune chronic active hepatitis (McFarlane et al. Lancet, 335, 754–757, 1990; Boudart et al. Lancet, 336, 63, 1990).

In an attempt to improve the sensitivity and specificity of the assays based on C100-3, a recombinant immunoblot assay (RIBA; Chiron-Ortho) has been developed. This test employs two HCV antigens; the recombinant HCV protein C100-3 (which is also called C-100) and the 5-1-1 fragment of C-100 (this gene product covers the C-terminal end of $NS_3$ and a portion of the N-terminal end of $NS_4$). SOD is used as a control. The 5-1-1 antigen is produced in *E. coli* as an SOD fusion. The C-100 peptide is produced in yeast, also as an SOD fusion. Using RIBA to confirm ELISA screening (using C100-3) of a low-risk population, specifically United States blood donors, only 19% of all ELISA repeat positive samples were also found positive by RIBA and 20% were indeterminate (Menitove et al. Lancet, 336, 243–244, 1990).

More recently, another dot-blot assay for HCV was developed by Abbott Laboratories. In this assay, four purified recombinant antigens are spotted on discrete locations on a piece of nitrocellulose paper. One antigen (SOD-C-100) is produced in yeast cells and the other three (C-100, HCV core protein and 33c) are produced in *E. coli* as fusions with CMP-KDO synthetase (CKS). The 33c antigen includes a large portion of the $NS_3$ protein. Mimms et al. (Lancet, 336, 1590–1591, 1990) have reported results obtained when this test was used on 153 samples found to be HCV positive by ELISA with C100-3. Only half (75) of the samples were found reactive with the two C-100 gene products—the SOD-C100-3 fusion and the C-100-CKS fusion. The other samples either did not react with any of the four antigens (62) or reacted non-specifically with SOD-C-100 fusion produced in yeast (16).

From the above it can be seen that the recombinant antigen based HCV diagnostic tests now available display poor sensitivity and poor selectivity. They miss a large proportion (15% to 33%) of the chronic cases of HCV and a larger proportion (70% to 90%) of the acute cases. Some 50% of the samples detected are false positives. Furthermore, immunoblot assays are too expensive and laborious for routine screening in blood banks. There is, thus, a definite need to develop a more sensitive and more specific test for the diagnosis of HCV infections.

SUMMARY OF THE INVENTION

This invention solves the above problems. It provides an HCV diagnostic test based on specific HCV peptides and mixtures thereof.

The peptides of this invention are selected from the group consisting of:

| (i) | | |
|---|---|---|
| (SEQ ID NO:1) | a-MSTNPKPQRKTKRNTNRRPQDVKFPG-b | (BCH-423) |
| (SEQ ID NO:5) | a-PQDVKFPGGGQIV-b | (BCH-436) |
| (SEQ ID NO:6) | a-KRNTNRRPQDVKFPGGGQIV-b | (BCH-437) |
| (SEQ ID NO:7) | a-KPQRKTKRNTNRRPQDVKFPGGGQIV-b | (BCH-438) |
| (SEQ ID NO:8) | a-MSTNPKPQRKTKRNTNRRPQDVKFPGGGQIV-b | (BCH-439) |
| (SEQ ID NO:10) | a-RGSRPSWGPNDPRRRSRNLGKVIDTLT-b | (BCH-443) |
| (SEQ ID NO:11) | a-KFPGGGQIVGGVYLLPRRGPRLGV-b | (BCH-446) |
| (SEQ ID NO:12) | a-RGRRQPIPKARRPEGRTWAQPGY-b | (BCH-448) |
| (SEQ ID NO:14) | a-GPRLGVRATRKTSERSQPRGRRQPI-b | (BCH-461) |
| (SEQ ID NO:13) | a-SSIVYEAADVIMHAPGSVPSVR-b | (BCH-458) | and analogues thereof;
wherein:
a is an amino terminus, one to eight amino acids or a substituent effective to facilitate coupling or to improve the immunogenic or antigenic activity of the peptide; and
b is a carboxy terminus, one to eight amino acids or a substituent effective to facilitate coupling or to improve the immunogenic or antigenic activity of the peptide; and
(ii) tandem peptides having the formula:

$$a - X - c - Z - b$$

wherein:
X and Z are independently selected from the group of amino acid sequences consisting of:

| (SEQ ID NO:1) | -MSTNPKPQRKTKRNTNRRPQDVKFPG- | (BCH-423) |
|---|---|---|
| (SEQ ID NO:5) | -PQDVKFPGGGQIV- | (BCH-436) |
| (SEQ ID NO:6) | -KRNTNRRPQDVKFPGGGQIV- | (BCH-437) |
| (SEQ ID NO:7) | -KPQRKTKRNTNRRPQDVKFPGGGQIV- | (BCH-438) |
| (SEQ ID NO:8) | -MSTNPKPQRKTKRNTNRRPQDVKFPGGGQIV- | (BCH-439) |
| (SEQ ID NO:10) | -RGSRPSWGPNDPRRRSRNLGKVIDTLT- | (BCH-443) |
| (SEQ ID NO:11) | -KFPGGGQIVGGVYLLPRRGPRLGV- | (BCH-446) |
| (SEQ ID NO:12) | -RGRRQPIPKARRPEGRTWAQPGY- | (BCH-448) |
| (SEQ ID NO:14) | -GPRLGVRATRKTSERSQPRGRRQPI- | (BCH-461) |
| (SEQ ID NO:13) | -SSIVYEAADVIMHAPGSVPSVR- | (BCH-458) | analogues thereof and fragments thereof comprising blocks of at least six consecutive amino acids of the amino acid sequence of X and Z and their analogues;

a and b are as defined above; and c is a linker of one or two amino acids or a substituent effective to facilitate coupling of the two peptides of the tandem or to improve the immunogenic or antigenic activity of the tandem peptide.

The peptides and mixtures thereof of this invention are useful for the screening of blood and body fluids for HCV infection and in the preparation of safe, effective vaccines against HCV. For example, the peptides of this invention and mixtures thereof are useful in a wide variety of specific binding assays for the detection of antibodies to HCV, as immunogens for eliciting antibodies useful for the detection of HCV antigens and in the preparation of vaccines against HCV viral infections.

BRIEF DESCRIPTION OF THE DRAWINGS

FIG. 1 depicts the amino acid sequence (SEQ ID NO:16) of the putative core gene product of HCV as described in Takeuchi et al. Nucleic Acids Res., 18, 4626, 1990).

FIG. 2 depicts the amino acid sequence (SEQ ID NO:17) of the putative envelope gene product as described in Takeuchi et al (supra).

FIG. 3 depicts the amino acid sequences (SEQ ID NOS:1–15) of the peptides of this invention and various other peptides prepared for comparative purposes. The location of the peptides in the sequences of FIGS. 1 and 2 are also indicated. The cysteine residue in positions 207, 226 and 229 (BCH-427 (SEQ ID NO: 2), BCH-429 (SEQ ID NO: 3) and BCH-458 (SEQ ID NO: 13)) was replaced by a serine residue.

In FIGS. 1–3, the amino acid residues of the sequences are given using the following single letter code: A=ala, C=cys, D=asp, E=glu, F=phe, G=gly, H=his, I=ile, K=lys, L=leu, M=met, N=asn, P=pro, Q=gln, R=arg, S=ser, T=thr, V=val, W=trp, Y=tyr.

DESCRIPTION OF THE INVENTION

The present invention provides novel peptides and analogues thereof corresponding to immunodominant regions of the putative core gene products of HCV. One peptide covering a reactive region of the putative envelope protein of HCV is also described. The present invention also provides mixtures and chemical combinations (tandems) of these peptides and analogues. As will be plain from the following description, these peptides, analogues, mixtures and tandems are useful in a wide variety of diagnostic and preventive methods, means and compositions with respect to HCV and the infections caused by it.

As set forth above, the peptides of this invention are selected from the group consisting of:

| (i) | | |
|---|---|---|
| (SEQ ID NO:1) | a-MSTNPKPQRKTKRNTNRRPQDVKFPG-b | (BCH-423) |
| (SEQ ID NO:5) | a-PQDVKFPGGGQIV-b | (BCH-436) |
| (SEQ ID NO:6) | a-KRNTNRRPQDVKFPGGGQIV-b | (BCH-437) |
| (SEQ ID NO:7) | a-KPQRKTKRNTNRRPQDVKFPGGGQIV-b | (BCH-438) |
| (SEQ ID NO:8) | a-MSTNPKPQRKTKRNTNRRPQDVKFPGGGQIV-b | (BCH-439) |
| (SEQ ID NO:10) | a-RGSRPSWGPNDPRRRSRNLGKVIDTLT-b | (BCH-443) |
| (SEQ ID NO:11) | a-KFPGGGQIVGGVYLLPRRGPRLGV-b | (BCH-446) |
| (SEQ ID NO:12) | a-RGRRQPIPKARRPEGRTWAQPGY-b | (BCH-448) |
| (SEQ ID NO:14) | a-GPRLGVRATRKTSERSQPRGRRQPI-b | (BCH-461) |
| (SEQ ID NO:13) | a-SSIVYEAADVIMHAPGSVPSVR-b | (BCH-458). | and analogues thereof wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide; and (ii) tandem peptides having the formula:

$$a - X - c - Z - b$$

wherein:

X and Z are independently selected from the group of amino acid sequences consisting of:

| (SEQ ID NO:1) | -MSTNPKPQRKTKRNTNRRPQDVKFPG- | (BCH-423) |
|---|---|---|
| (SEQ ID NO:5) | -PQDVKFPGGGQIV- | (BCH-436) |
| (SEQ ID NO:6) | -KRNTNRRPQDVKFPGGGQIV- | (BCH-437) |
| (SEQ ID NO:7) | -KPQRKTKRNTNRRPQDVKFPGGGQIV- | (BCH-438) |
| (SEQ ID NO:8) | -MSTNPKPQRKTKRNTNRRPQDVKFPGGGQIV- | (BCH-439) |
| (SEQ ID NO:10) | -RGSRPSWGPNDPRRRSRNLGKVIDTLT- | (BCH-443) |
| (SEQ ID NO:11) | -KFPGGGQIVGGVYLLPRRGPRLGV- | (BCH-446) |
| (SEQ ID NO:12) | -RGRRQPIPKARRPEGRTWAQPGY- | (BCH-448) |
| (SEQ ID NO:14) | -GPRLGVRATRKTSERSQPRGRRQPI- | (BCH-461) |
| (SEQ ID NO:13) | -SSIVYEAADVIMHAPGSVPSVR- | (BCH-458) | analogues thereof and fragments thereof comprising blocks of at least six consecutive amino acids of the amino acid sequence of X and Y and their analogues;

a and b are as defined above; and c is a linker of one or two amino acids or a substituent effective to facilitate coupling of the two peptides of the tandem or to improve the immunogenic or antigenic activity of the tandem peptide.

As used herein, "analogues" denote amino acid insertions, deletions, substitutions and modifications at one or more sites in the peptide chain in that portion of it that consists of the block of the naturally occurring HCV amino acid sequences.

Preferred modifications and substitutions to the native amino acid sequence of the peptides of this invention are conservative ones (i.e., those having minimal influence on the secondary structure and hydropathic nature of the peptide). These include substitutions such as those described by Dayhoff in the Atlas of Protein Sequence and Structure 5, 1978 and by Argos in EMBO J., 8, 779–785, 1989. For example, amino acids belonging to one of the following groups represent conservative changes: ala, pro, gly, glu, asp, gln, asn, ser, thr; cys, ser, tyr, thr; val, ile, leu, met, ala, phe; lys, arg, his; and phe, tyr, trp, his.

In like manner, methionine, an amino acid which is prone to oxidation, may be replaced in the peptides of this invention by norleucine. The preferred substitutions also include substitutions of D-isomers for the corresponding L-amino acids.

The term "amino acid" as employed in this description (e.g., in the definition of a and b and analogues) except when referring to the native amino acid sequence of the gene products of HCV, encompasses all of the natural amino acids, those amino acids in their D-configurations, and the known non-native, synthetic, and modified amino acids, such as homocysteine, ornithine, norleucine and β-valine.

As set forth briefly above, it is often useful and certainly within the scope of this invention to modify the peptides of this invention in order to make the chosen peptide more useful as an immunodiagnostic reagent or as an active ingredient of a vaccine. Such changes, for example, include:

— addition of a cysteine residue to one or both terminals in order to facilitate coupling of the peptide to a suitable carrier with heterobi-functional cross-linking reagents, such as sulfosuccinimidyl-4-(p-maleimidophenyl) butyrate. Preferred reagents for effecting such linkages are sulfosuccinimidyl-sulfosuccinimidyl-4-(N-maleimidomethyl)cyclohexane-1-carboxylate and N-succinimidyl-3-(2-pyridyldithio)propionate;

— addition of 1 to 8 additional amino acids at one or both terminals of the peptide to facilitate linking of the peptides to each other, for coupling to a support or larger peptide or protein or for modifying the physical or chemical properties of the peptide. Examples of such changes are the addition of N- or C-terminal tyrosine, glutamic acid or aspartic acid as linkers via an esterification reaction and lysine which can be linked via Schiff base or amide formation. As described above, such additional amino acids may include any of the natural amino acids, those amino acids in their D-configurations and the known non-native, synthetic and modified amino acids; and — derivatization of one or both terminals of the peptide by, for example, acylation or amidation. These modifications result in changes in the net charge on the peptide and can also facilitate covalent linking of the peptide to a solid support, a carrier or another peptide. Examples of the substituents effective to facilitate coupling or to improve the immunogenicity or antigenic activity of the peptide are $C_2$–$C_{16}$ acyl groups, polyethylene glycol and phospholipids.

As reflected in (ii) above, it is within the scope of this invention to employ tandem peptides. These peptides may be homopolymers or copolymers. Physical mixtures of the peptides and tandem peptides of this invention are also within its scope.

The preferred peptides of this invention are BCH-423 (SEQ ID NO:1), BCH-437 (SEQ ID NO:6), BCH-438 (SEQ ID NO:7) and BCH-439 (SEQ ID NO:8). The most preferred peptide of this invention is BCH-438 (SEQ ID NO:7). The preferred peptide mixture and tandems of this invention contains at least BCH-438 (SEQ ID NO:7). More preferably, they contain BCH-438 (SEQ ID NO:7) and BCH-461 (SEQ ID NO:14).

An unexpected advantage of the peptides and mixtures of this invention is their high sensitivity. They are capable of detecting HCV-specific antibodies in the majority and sometimes in all of confirmed seropositive samples present in commercial panels sold for the assessment of the performance of HCV diagnostic kits. Another advantage of the peptides and mixtures of this invention is their high specificity. For example, using BCH-437 (SEQ ID NO:6) or BCH-438 (SEQ ID NO:7) no false-positives were recorded when sixty-three samples taken from the normal blood donor population were tested.

In addition to their use in HCV diagnostic means, methods and compositions the peptides of this invention and mixtures thereof are also useful in vaccines against HCV infections.

To prepare the novel peptides of this invention any of the conventional peptide production methodologies may be used. These include synthesis, recombinant DNA technology and combinations thereof. We prefer solid phase synthesis.

In that synthetic approach, the resin support may be any suitable resin conventionally employed in the art for the solid phase preparation of peptides. Preferably, it is a p-benzyloxy-alcohol polystyrene or p-methylbenzyhydrylamine resin. Following the coupling of the first protected amino acid to the resin support, the amino protecting group is removed by standard methods conventionally employed in the art. After removal of the amino protecting group, the remaining protected amino acids and, if necessary, side chain protected amino acids are coupled, sequentially, in the desired order to obtain the chosen peptide. Alternatively, multiple amino acid groups may be coupled using solution methodology prior to coupling with the resin-supported amino acid sequence.

The selection of an appropriate coupling reagent follows established art. For instance, suitable coupling reagents are N,N'-diisopropylcarbodiimide or N,N'-dicyclohexylcarbodiimide (DCC) or preferably, benzotriazol-1-yloxy-tris (dimethylamino) phosphonium hexafluoro-phosphate either alone more or preferably in the presence of 1-hydroxybenzotriazole. Another useful coupling procedure employs preformed symmetrical anhydrides of protected amino acids.

The necessary α-amino protecting group employed for each amino acid introduced onto the growing polypeptide chain is preferably 9-fluorenylmethyloxycarbonyl (FMOC), although any other suitable protecting group may be employed as long as it does not degrade under the coupling conditions and is readily and selectively removable in the presence of any other protecting group already present in the growing peptide chain.

The criteria for selecting protecting groups for the side chain amino acids are: (a) stability of the protecting group to the various reagents under reaction conditions selective for the removal of the α-amino protecting group at each step of the synthesis; (b) retention of the protecting group's strategic properties (i.e., not be split off under coupling conditions) and (c) removability of protecting group easily upon conclusion of the peptide synthesis and under conditions that do not otherwise affect the peptide structure.

The fully protected resin-supported peptides are preferably cleaved from the p-benzyloxy alcohol resin with 50% to 60% solution of trifluoroacetic acid in methylene chloride for 1 to 6 hours at room temperature in the presence of appropriate scavengers such as anisole, thioanisole, ethyl methyl sulfide, 1,2-ethanedithiol and related reagents. Simultaneously, most acid labile side chain protecting groups are removed. More acid resistant protecting groups are typically removed by HF treatment.

The peptides of the present invention are useful as diagnostic reagents for the detection and quantification of HCV associated antibodies in accordance with methods well-known in the art. These include ELISA, hemagglutination, single-dot and multi-dot assay methods (e.g., RIBA).

A preferred convenient and classical technique for the determination of antibodies against HCV using a peptide or a peptide mixture of this invention is an enzyme-linked immunosorbent assay (ELISA). In this assay, for example, a peptide or mixture of this invention is adsorbed onto, or covalently coupled to, the wells of a microtiter plate. The wells are then treated with the sera or analyte to be tested. After washing, anti-human IgG or anti-human IgM labeled with peroxidase is added to the wells. The determination of the peroxidase is performed with a corresponding substrate, e.g., 3,3',5,5'-tetramethylbenzidine. Without departing from the usefulness of this illustrative assay, the peroxidase can be exchanged by another label, e.g., by a radioactive, fluorescence, chemiluminescence or infra-red emitting label.

Another method for the determination of the presence of antibodies against HCV in a test sample or sera with the peptides and mixtures of this invention is an enzyme immunological test according to the so-called "Double-Antigen-Sandwich-Assay". This method is based on the work of Maiolini, as described in Immunological Methods, 20, 25–34, 1978. According to this method, the serum or other analyte to be tested is contacted with a solid phase on which a peptide of this invention has been coated (capture layer) and with a peptide of this invention which has been labeled with peroxidase or other signal (probe layer).

The immunological reaction can be performed in one or two steps. If the immunological reaction is performed in two steps, then a washing step is typically carried out between the two incubations. After the immunological reaction or reactions, a washing step is also usually performed. Thereafter, the peroxidase or other signal is determined, e.g., using o-phenylene diamine for peroxidase. Other enzymes and chromogens, including those already described, can also be employed in this assay.

Suitable solid phases for use in the above-described assays and assay methods include organic and inorganic polymers, e.g., amylases, dextrans, natural or modified celluloses, polyethylene, polystyrene, polyacrylamides, agaroses, magnetite, porous glass powder, polyvinyldiene fluoride (kynar) and latex, the inner wall of test vessels (i.e., test tubes, titer plates or cuvettes of glass or artificial material) as well as the surface of solid bodies (i.e., rods of glass and artificial material, rods with terminal thickening, rods with terminal lobes or lamellae). Spheres of glass and artificial material are especially suitable as solid phase carriers.

The peptides of this invention and mixtures of them are not only useful in the determination and quantification of antibodies against HCV. They are also useful for the determination and quantification of HCV antigens themselves because the peptides of this invention, either free, polymerized or conjugated to an appropriate carrier are useful in eliciting antibodies, in particular and preferably monoclonal antibodies, immunologically cross reactive to antigens of HCV. Such antibodies, for example, can be produced by injecting a mammalian or avian animal with a sufficient amount of the peptide to elicit the desired immune response and recovering said antibodies from the serum of said animals. Suitable host animals for eliciting antibodies include, for example, rabbits, horses, goats, guinea pigs, rats, mice, cows, sheep and hens. Preferably, hybridomas producing the desired monoclonal antibodies are prepared using the peptides of this invention and conventional techniques.

For example, the well-known Kohler and Milstein technique for producing monoclonal antibodies may be used. In order to distinguish monoclonal antibodies which are directed against the same antigen, but against different epitopes, the method of Stähli et al. (J. of Immunological Methods, 32, 297–304, 1980) can be used.

Various methods which are generally known can be employed in the determination or quantification of HCV or a portion thereof using the above antibodies. In one such procedure, known amounts of a serum sample or other analyte to be assayed, a radiolabeled peptide or mixture of this invention and an unlabeled peptide or mixture of this invention are mixed together, a given amount of an antibody to a peptide of this invention, preferably a monoclonal antibody, is added and the mixture allowed to stand. The resulting antibody/antigen complex is then separated from the unbound reagents by procedures known in the art such as treatment with ammonium sulphate, polyethylene glycol, a second antibody either in excess or bound to an insoluble support, or dextran-coated charcoal.

The concentration of the labeled peptide is then determined in either the bound or unbound phase and the HCV antigen content of the sample determined by comparing the level of labeled component to a standard curve in a manner known per se.

Another suitable method for using these antibodies in assays is the "Double-Antibody-Sandwich-Assay". According to this assay, the sample to be tested is treated with two different antibodies, e.g., raised by immunizing different animals, e.g., sheep and rabbits with a peptide of this invention or a mixture or combination thereof. One of the antibodies is labeled and the other is coated on a solid phase. The preferred solid phase is a plastic bead and the preferred label is horse-radish peroxidase.

Typically in the "Double-Antibody-Sandwich-Assay", the sample is incubated with the solid phase antibody and the labeled antibody. However, it is also possible to contact the sample first with the solid phase antibody and, then after an optional washing, to contact the sample with the labeled antibody. Preferably, however, the sample is treated together with the solid phase and the labeled antibody. After the immunological reaction(s), the mixture is washed and the label is determined according to procedures known in the art. In the case where peroxidase is used as the label, the determination maybe performed using a substrate, e.g., with o-phenylene diamine or with tetramethylbenzidine. The amount of the labeled component is proportional to the amount of the antigen(s) present in the analyte or serum sample.

The methods and assays for the determination and quantification of HCV antigens or antibodies against this virus, as described above, can also be conducted in suitable test kits characterized by a peptide or mixture of this invention, or antibodies against HCV elicited by those peptides and mixtures.

As described above, the peptides and mixtures of this invention are also useful as the active component of vaccines capable of inducing protective immunity against HCV in hosts susceptible to infection with this virus. Routes of administration, antigen doses and number and frequency of injections will vary from individual to individual and will parallel those currently being used in providing immunity to other viral infections. For example, the vaccines of this invention are pharmaceutically acceptable compositions containing at least one peptide or mixture of this invention in an amount effective in a mammal, including a human, treated with that composition, to raise antibodies sufficient to protect the treated mammal from an HCV infection for a period of time.

The vaccines are prepared in accordance with known methods. The vaccine compositions of this invention may be conveniently and conventionally combined with physiologically acceptable carrier materials, such as pharmaceutical grade saline, tetanus toxoid, and keyhole limpet hemocyanin. The vaccine compositions of this invention may also contain adjuvants or other enhancers of immune response, such as alum preparations, liposomes or immunomodulators. Furthermore, these vaccine compositions may comprise other antigens to provide immunity against other viruses (e.g., Hepatitis B virus, HIV-1 and HIV-2, cytomegalovirus) or pathogens in addition to HCV. The amount of these other antigens is again dependent on the mammal to be treated and the course of the disease. However, the antigen should be present in an amount effective to raise antibodies sufficient to protect the treated mammal from that pathogen or virus for a period of time.

General procedures for the synthesis and utilization of the peptides of this invention are provided below.

PROCEDURE 1

Preparation of Resins Carrying the N-FMOC Protected Amino Acid Residue

The desired N-FMOC protected amino acid residue in a mixture of methylene chloride ($CH_2Cl_2$) and dimethylformamide (DMF) (4:1) was added to a suspension of p-benzyloxy alcohol resin in $CH_2Cl_2$:DMF (4:1) at 0° C. The mixture was stirred manually for a few seconds and then treated with N,N'-dicyclohexyl-carbodiimide (DCC) followed by a catalytic amount of 4-(dimethylamino) pyridine. The mixture was stirred at 0° C. for an additional 30 minutes and then at room temperature overnight. The filtered resin was washed successively with $CH_2Cl_2$, DMF and isopropanol (3 washes each) and finally, with $CH_2Cl_2$. The resin was suspended in $CH_2Cl_2$, chilled in an ice bath and redistilled pyridine was added to the stirred suspension, followed by benzoyl chloride. Stirring was continued at 0° C. for 30 minutes and then at room temperature for 60 minutes. After filtration, the resin was washed successively with $CH_2Cl_2$, DMF and isopropanol (3 washes each) and finally with petroleum ether (twice) before being dried under high vacuum to a constant weight. Spectrophotometric determination of substitution according to Meienhofer et al. (Int. J. Peptide Protein Res., 13, 35, 1979) indicates the degree of substitution on the resin.

PROCEDURE 2

Coupling of Subsequent Amino Acids

The resin carrying the N-FMOC protected first amino acid residue was placed in a reaction vessel of a Biosearch 9600 Peptide Synthesizer and treated as follows:

1) Washed with DMF (4 times for 20 sec. each)
2) Prewashed with a 30% solution of piperidine in DMF (3 min.)
3) Deprotected with a 30% solution of piperidine in DMF (7 min.)

4) Washed with DMF (8 times for 20 sec. each)

5) Checked for free amino groups—Kaiser Test (must be positive)

6) The peptide resin was then gently shaken for 1 or 2 hrs with 8 equivalents of the desired FMOC-protected amino acid and 1-hydroxybenzotriazole and benzotriazol-1-yloxy-tris(dimethyl-amino) phosphonium hexafluorophosphate all dissolved in dry redistilled DMF containing 16 equivalents of 4-methylmorpholine.

7) Washed with DMF (6 times for 20 sec. each)

After step 7, an aliquot was taken for a ninhydrin test. If the test was negative, the procedure was repeated from step 1 for coupling of the next amino acid. If the test was positive or slightly positive, steps 6 and 7 were repeated.

The above scheme may be used for coupling each of the amino acids of the peptides described in this invention. N-protection with FMOC may also be used with any of the remaining amino acids throughout the synthesis.

Radiolabeled peptides may be prepared by incorporation of a tritiated amino acid using the above coupling protocol.

After the addition of the last amino acid, the N-FMOC of the N-terminal residue is removed by going back to steps 1–7 of the above scheme. The peptide resin is washed with $CH_2Cl_2$ and dried in vacuo to give the crude protected peptide.

PROCEDURE 3

Deprotection and Cleavage of the Peptides from the Resin

The protected peptide-resin was suspended in a 55% solution of trifluoroacetic acid (TFA) in $CH_2Cl_2$, containing 2.5% ethanedithiol and 2.5% anisole. The mixture was flushed with $N_2$ and stirred for 1.5 hours at room temperature. The mixture was filtered and the resin washed with $CH_2Cl_2$. The resin was treated again with 20% TFA in $CH_2Cl_2$ for 5 minutes at room temperature. The mixture was filtered and the resin washed with 20% TFA in $CH_2Cl_2$ and then washed with $CH_2Cl_2$. The combined filtrates were evaporated in vacuo below 35° C. and the residue washed several times with dry dimethyl ether. The solid was dissolved in 10% aqueous acetic acid and lyophilized to afford the crude product.

The peptides containing arg and cys residues are further deprotected by HF treatment at 0° C. for 1 hour in the presence of anisole and dimethylsulfide. The peptides were extracted with 10% aqueous acetic acid, washed with dimethyl ether and lyophilized to afford the crude peptides.

PROCEDURE 4

Purification of Peptides

The crude peptides were purified by preparative HPLC on a Vydac column (2.5×25 mm) of $C_{18}$ or $C_4$ reverse phase packing with a gradient of the mobile phase. The effluent was monitored at 220 nm and subsequently by analytical HPLC. Relevant fractions were pooled, evaporated and lyophilized. The identity of the synthetic peptides was verified by analytical reverse phase chromatography and by amino acid analysis.

PROCEDURE 5

Conjugation of Peptides to Bovine Serum Albumin (BSA) or Keyhole Limpet Hemocyanin (KLH)

Peptides were conjugated to BSA or KLH previously derivatized with either sulfosuccinimidyl 4-(p-maleimidophenyl) butyrate (Sulfo-SMPB) or sulfosuccinimidyl 4-(N-maleimidomethyl) cyclohexane-1-carboxylate (Sulfo-SMCC).

An aqueous solution of sulfo-SMPB or sulfo-SMCC (Pierce Chemicals) was added to a solution of BSA or KLH in 0.02M sodium phosphate buffer (pH 7.0). The mixture was shaken at room temperature for 45 minutes and the activated carrier immediately applied to a Sephadex G-25 column equilibrated with 0.1M sodium phosphate buffer (pH 6.0) at 4° C.

The fractions of the first peak absorbance (280 nm) corresponding to activated carrier were combined in a round bottom flask to which was added a solution of peptide in 0.05M sodium phosphate buffer (pH 6.2). The mixture was thoroughly flushed with $N_2$ and incubated overnight at room temperature. The coupling efficiency was monitored using $^3$H-labeled peptide and by amino acid analysis of the conjugate.

PROCEDURE 6

Detection of Antibodies to HCV by an Enzyme Linked Immunosorbent Assay (ELISA)

Each well of the microtiter plate was saturated with 100 μl of a solution (filtered 0.05M carbonate-bicarbonate buffer, pH 9.4±0.2) containing a peptide or mixture of peptides (10 μg/ml) and left overnight. Preferably, we use an Oster Bay Versafill dispensing system to fill the wells. The wells were emptied (preferably by aspiration) and washed twice with a washing buffer (NaCl, 0.15M; $NaH_2PO_4$, 0.060M; thimerosal, 0.01% and Tween 20, 0.05%; pH 7.4 (0.3 mL/well)). The wells were then saturated with 0.35 ml of washing buffer for 1 hour at 37° C. and washed once with the same buffer without Tween 20. After again drying for 1 hour at 37° C., the wells were ready for use. Serum samples to be analyzed were diluted with specimen buffer (sodium phosphate, 6 mM; NaCl, 0.15M; BSA, 2%; peptone, 1.5%; benzamidine, 80 mM; Tween 20, 1%; heat-inactivated goat serum, 40%; thimerosal 0.01%, final pH is equal to 7.2). The wells were rinsed with washing buffer prior to the addition of the diluted serum sample (0.1 ml). These were left to incubate for 30 minutes at room temperature. The wells were then emptied, washed twice rapidly and then once for two minutes with washing buffer. The conjugate solution (peroxidase labeled affinity purified goat antibody to human IgG, 0.5 mg in 5 ml 50% glycerol) diluted with 1% w/v bovine serum albumin in a solution containing Tris, 0.05M; NaCl, 0.5M; Tween 20, 0.05%; thimerosal 0.01% (pH 7.2) was added to each well (0.1 ml) and incubated for 30 minutes at room temperature. The wells were then emptied and washed five times with the washing buffer. The substrate solution (3,3',5,5'-tetramethyl-benzidine) (8 mg per ml of DMSO) was diluted with 100 volumes 0.1M citrate-acetate buffer (pH 5.6) containing 0.1% v/v of 30% $H_2O_2$ and added to each well (0.1 ml per well). After 10 minutes, the contents of each well were treated with 0.1 ml 2N $H_2SO_4$ and the optical density read at 450 nm. All determinations were done in duplicate.

Using general procedures substantially as described above, the specific peptides outlined in FIG. 3 were prepared. These peptides were then evaluated for their ability to detect HCV-specific antibodies.

EXPERIMENT 1

In Experiment 1 individual peptides were solubilized at a final concentration of 10 μg/ml in 0.05M sodium carbonate-bicarbonate buffer (pH 9.6). The wells were then treated as described in procedure 6.

A panel of 25 anti-HCV reactive serum and plasma samples from Boston Biomedica Inc. (BBI) was used. Table 1 illustrates the antigenic reactivity of nine synthetic peptides covering different sequences of the core protein of HCV.

BCH-423 (SEQ ID NO:1), BCH-437 (SEQ ID NO:6), BCH-438 (SEQ ID NO:7) and BCH-439 (SEQ ID NO:8), all of which could detect at least 24 out of 25 (≧96%) anti-HCV reactive samples. Further experiments were, thus, done using BCH-423 (SEQ ID NO:1), BCH-437 (SEQ ID NO:6),

TABLE 1

| | EIA WITH SYNTHETIC PEPTIDE | | | | | | | | |
|---|---|---|---|---|---|---|---|---|---|
| Sample No. | BCH-423 (SEQ ID NO:1) | BCH-436 (SEQ ID NO:5) | BCH-437 (SEQ ID NO:6) | BCH-438 (SEQ ID NO:7) | BCH-439 (SEQ ID NO:8) | BCH-443 (SEQ ID NO:10) | BCH-446 (SEQ ID NO:11) | BCH-448 (SEQ ID NO:12) | BCH-461 (SEQ ID NO:14) |
| 1801-1 | >16 | >22 | >22 | >19 | >18 | >22 | >22 | >21 | >18 |
| 1801-2 | >16 | >22 | >22 | >19 | >18 | 7.8 | >22 | >21 | >18 |
| 1801-3 | 13 | 0.8 | 10 | 15.2 | 16 | 0.6 | 0.4 | 0.2 | 0.5 |
| 1801-12 | >16 | 2.6 | >22 | >19 | >18 | 1.6 | >22 | 7.0 | 1.6 |
| 1801-19 | >16 | 10 | >22 | >19 | >18 | 6.7 | >22 | 5.7 | 4.0 |
| 1801-20 | >16 | 4.4 | >22 | >19 | >18 | 4.5 | 21 | 5.1 | 6.9 |
| 1801-25 | 15 | 1.7 | >22 | >19 | >18 | 1.1 | >22 | 0.1 | 0.3 |
| 1801-30 | >16 | 1.6 | >22 | >19 | >18 | 1.2 | >22 | 0.1 | 0.3 |
| 1801-31 | >16 | 15 | >22 | >19 | >18 | 15 | 15 | 16 | 13 |
| 1801-40 | 1.7 | 0.2 | 0.5 | 0.9 | 2.1 | 0.3 | 0.0 | 0.1 | 0.4 |
| 1801-43 | >16 | >22 | >22 | >19 | >18 | 19 | >22 | >21 | >18 |
| 1801-58 | >16 | >22 | >22 | >19 | >18 | 2.5 | >22 | 5.0 | >18 |
| 1801-59 | 0.2 | 0.3 | 1.6 | 3.0 | 3.8 | 0.2 | 0.0 | 0.2 | 0.2 |
| 1801-61 | >16 | >22 | >22 | >19 | >18 | 2.3 | >22 | 4.7 | >18 |
| 1801-63 | >16 | >22 | >22 | >19 | >18 | 2.1 | >22 | 4.4 | >18 |
| 1801-81 | >16 | 10.5 | >22 | >19 | >18 | 7.6 | 16 | 8.0 | >18 |
| 1801-82 | >16 | >22 | >22 | >19 | >18 | >22 | >22 | >21 | >18 |
| 1801-83 | >16 | >22 | >22 | >19 | >18 | >22 | >22 | >21 | >18 |
| 1801-86 | >16 | 20 | >22 | >19 | >18 | 8.8 | 21 | 13 | >18 |
| 1801-90 | >16 | 2.9 | >22 | >19 | >18 | 4.0 | >22 | 0.4 | 2.3 |
| 3210-119 | >16 | 8.4 | >22 | >19 | >18 | 2.5 | >22 | 1.7 | 4.4 |
| 3210-127 | >16 | 1.7 | >22 | >19 | >18 | 7.2 | >22 | 0.9 | 1.5 |
| 3210-223 | >16 | 3.1 | 14 | >19 | >18 | 2.5 | >22 | 1.0 | 1.8 |
| 3210-464 | 5.6 | 0.9 | 8.0 | 9.7 | 9.7 | 0.4 | 1.1 | 1.0 | 1.0 |
| 3210-748 | >16 | >22 | >22 | >19 | >18 | >22 | >22 | >21 | >18 |

The results represent signal to cutoff ratios. The cutoff is the average absorbency obtained with plasma samples drawn from three normal blood donors to which a value of 0.100 is added. A ratio ≧1.0 indicates a reactive sample. BCH-448 (SEQ ID NO:12) and BCH-461 (SEQ ID NO:14) were able to detect the presence of anti-HCV antibodies in 72% (18/25) and 80% (20/25), respectively, of the samples tested. More impressively, BCH-436 (SEQ ID NO:5) and BCH-443 (SEQ ID NO:10) detected antibodies in 84% (21/25) of the samples and BCH-446 (SEQ ID NO:11) detected antibodies in 88% (22/25) of the samples screened. The most impressive results, however, were observed using BCH-438 (SEQ ID NO:7) and BCH-439 (SEQ ID NO:8) (see Experiment 3).

EXPERIMENT 2

Synthetic peptides with sequences covering portions of the putative envelope protein were tested as described above and using the same panel of 25 samples.

The results represent signal to cutoff ratios calculated as described above and are displayed in Table 2.

TABLE 2

| | EIA WITH SYNTHETIC PEPTIDE | | | | | |
|---|---|---|---|---|---|---|
| Sample No. | BCH-427 (SEQ ID NO:2) | BCH-458 (SEQ ID NO:13) | BCH-429 (SEQ ID NO:3) | BCH-440 (SEQ ID NO:9) | BCH-430 (SEQ ID NO:4) | BCH-464 (SEQ ID NO:15) |
| 1801-1 | 0.3 | 7.4 | 1.3 | 1.1 | 0.3 | 0.1 |
| 1801-2 | 0.1 | 8.2 | 3.3 | 1.5 | 0.3 | 0.1 |
| 1801-3 | 0.1 | 0.1 | 0.1 | 0.0 | 0.1 | 0.0 |
| 1801-12 | 0.1 | 0.9 | 0.2 | 0.0 | 0.1 | 0.0 |
| 1801-19 | 0.7 | 8.0 | 0.9 | 0.4 | 0.8 | 0.3 |
| 1801-20 | 0.2 | 0.7 | 0.2 | 0.2 | 0.2 | 0.1 |
| 1801-25 | 0.2 | 0.7 | 0.2 | 0.0 | 0.2 | 0.3 |
| 1801-30 | 0.2 | 0.7 | 0.2 | 0.0 | 0.3 | 0.4 |
| 1801-31 | 0.2 | 4.0 | 0.3 | 0.1 | 0.3 | 0.1 |
| 1801-40 | 0.3 | 0.1 | 0.5 | 0.1 | 0.2 | 0.1 |
| 1801-43 | 0.2 | >20 | 5.0 | 3.2 | 0.4 | 0.2 |
| 1801-58 | 0.1 | 7.9 | 0.4 | 0.3 | 0.3 | 0.0 |
| 1801-59 | 0.2 | 0.2 | 0.2 | 0.0 | 0.1 | 0.0 |
| 1801-61 | 0.1 | 8.6 | 0.3 | 0.2 | 0.2 | 0.1 |

TABLE 2-continued

| | EIA WITH SYNTHETIC PEPTIDE | | | | | |
|---|---|---|---|---|---|---|
| Sample No. | BCH-427 (SEQ ID NO:2) | BCH-458 (SEQ ID NO:13) | BCH-429 (SEQ ID NO:3) | BCH-440 (SEQ ID NO:9) | BCH-430 (SEQ ID NO:4) | BCH-464 (SEQ ID NO:15) |
| 1801-63 | 0.1 | 8.0 | 0.3 | 0.3 | 0.2 | 0.0 |
| 1801-81 | 1.7 | 3.4 | 0.4 | 0.4 | 0.2 | 0.1 |
| 1801-82 | 0.2 | 10.8 | 2.3 | 1.3 | 0.3 | 0.2 |
| 1801-83 | 0.3 | 16.5 | 2.4 | 1.5 | 1.0 | 0.2 |
| 1801-86 | 0.4 | 4.3 | 0.6 | 0.4 | 0.3 | 0.1 |
| 1801-90 | 0.3 | 1.2 | 0.4 | 0.2 | 0.3 | 0.8 |
| 3210-119 | 0.3 | 6.0 | 0.8 | 0.3 | 0.6 | 0.2 |
| 3210-127 | 0.3 | 1.8 | 0.8 | 0.2 | 1.1 | 0.1 |
| 3210-223 | 0.1 | 1.0 | 0.4 | 0.2 | 0.2 | 0.1 |
| 3210-464 | 0.1 | 0.3 | 0.1 | 0.1 | 0.1 | 0.1 |
| 3210-748 | 0.3 | >20 | 3.0 | 9.0 | 0.6 | 0.4 |

As shown in Table 2, synthetic peptides BCH-464 (SEQ ID NO:15), BCH-427 (SEQ ID NO:2) and BCH-430 (SEQ ID NO:4) are very poor antigens detecting respectively zero, one and two samples out of the panel of 25 specimens. BCH-429 (SEQ ID NO:3) and BCH-440 (SEQ ID NO:9) are also poor since they only detect 6 samples out of this 25 member panel. BCH-458 (SEQ ID NO:13), which covers a region adjacent to BCH-427 (SEQ ID NO:2) and partially overlaps with BCH-429 (SEQ ID NO:3), is the only reactive antigen, detecting 17 samples.

EXPERIMENT 3

The four best synthetic peptides identified in Experiment 1 were further tested on two series of well characterized samples sold by BBI. The first panel is composed of 25 anti-HCV mixed titer samples (PHV-201) and the second series includes 15 low titer anti-HCV serum and plasma samples (PHV-101). The results are displayed in Tables 3a and 3b, respectively.

TABLE 3a

| | EIA WITH SYNTHETIC PEPTIDE | | | | | |
|---|---|---|---|---|---|---|
| Sample No. | Abbott | Ortho | BCH-423 (SEQ ID NO:1) | BCH-437 (SEQ ID NO:6) | BCH-438 (SEQ ID NO:7) | BCH-439 (SEQ ID NO:8) |
| PHV-201-01 | 1.69(P) | 1.48(P) | >18 | >22 | >22 | >22 |
| PHV-201-02 | 3.67(P) | 5.66(P) | >18 | >22 | >22 | >22 |
| PHV-201-03 | 3.79(P) | 3.95(P) | >18 | >22 | >22 | >22 |
| PHV-201-04 | 0.27(N) | 0.18(N) | 0.39 | 0.11 | 0.10 | 0.15 |
| PHV-201-05 | 3.42(P) | 2.59(P) | >18 | >22 | >22 | >22 |
| PHV-201-06 | 3.71(P) | 4.81(P) | >18 | >22 | >22 | >22 |
| PHV-201-07 | 0.26(N) | 0.11(N) | 0.39 | 0.27 | 0.29 | 0.31 |
| PHV-201-08 | 1.52(P) | 1.24(I) | 1.17 | 1.63 | 3.53 | 2.54 |
| PHV-201-09 | 2.53(P) | 1.27(P) | >18 | >22 | >22 | >22 |
| PHV-201-10 | 2.17(P) | 2.74(I) | 12.38 | 0.33 | 1.59 | 0.87 |
| PHV-201-11 | 2.88(P) | 2.17(P) | >18 | >22 | >22 | >22 |
| PHV-201-12 | 3.64(P) | 4.77(P) | 14.92 | 15.51 | 20.39 | >22 |
| PHV-201-13 | 4.12(P) | 5.66(P) | >18 | >22 | >22 | >22 |
| PHV-201-14 | 2.67(P) | 4.30(P) | >18 | >22 | >22 | >22 |
| PHV-201-15 | 4.12(P) | 5.66(P) | >18 | >22 | >22 | >22 |
| PHV-201-16 | 4.12(P) | 5.66(P) | >18 | >22 | >22 | >22 |
| PHV-201-17 | 4.12(P) | 5.66(P) | >18 | >22 | >22 | >22 |
| PHV-201-18 | 3.54(P) | 3.94(P) | 14.46 | >22 | >22 | >22 |
| PHV-201-19 | 0.50(N) | 1.53(N) | 0.18 | 0.52 | 0.67 | 0.90 |
| PHV-201-20 | 2.61(P) | 2.38(P) | 1.11 | 1.72 | 1.90 | 2.34 |
| PHV-201-21 | 3.43(P) | 2.67(P) | >18 | >22 | >22 | >22 |
| PHV-201-22 | 1.72(P) | 1.69(P) | 13.69 | 13.63 | 19.48 | >22 |
| PHV-201-23 | 4.12(P) | 5.66(P) | >18 | >22 | >22 | >22 |

TABLE 3a-continued

| | EIA WITH SYNTHETIC PEPTIDE | | | | | |
|---|---|---|---|---|---|---|
| Sample No. | Abbott | Ortho | BCH-423 (SEQ ID NO:1) | BCH-437 (SEQ ID NO:6) | BCH-438 (SEQ ID NO:7) | BCH-439 (SEQ ID NO:8) |
| PHV-201-24 | 2.50(P) | 2.63(P) | >18 | >22 | >22 | >22 |
| PHV-201-25 | 4.12(P) | 5.66(P) | >18 | >22 | >22 | >22 |

TABLE 3b

| | EIA WITH SYNTHETIC PEPTIDE | | | | | |
|---|---|---|---|---|---|---|
| Sample No. | Abbott | Ortho | BCH-423 (SEQ ID NO:1) | BCH-437 (SEQ ID NO:6) | BCH-438 (SEQ ID NO:7) | BCH-439 (SEQ ID NO:8) |
| PHV-101-02 | 0.17(N) | 0.27(N) | 0.30 | 0.18 | 0.20 | 0.24 |
| PHV-101-03 | 1.88(P) | 1.32(N) | 1.51 | 0.63 | 1.30 | 1.61 |
| PHV-101-04 | 1.76(P) | 3.08(P) | >18 | >22 | >22 | >21 |
| PHV-101-05 | 3.40(P) | 2.17(N) | 2.03 | 0.85 | 2.04 | 2.73 |
| PHV-101-06 | 1.64(P) | 1.64(P) | >18 | >22 | >22 | >21 |
| PHV-101-07 | 2.28(P) | 1.62(P) | 17.3 | >22 | >22 | >21 |
| PHV-101-08 | 3.01(P) | 1.59(P) | >18 | >22 | >22 | >21 |
| PHV-101-09 | 1.86(P) | 1.12(P) | >18 | >22 | >22 | >21 |
| PHV-101-10 | 3.65(P) | 3.10(P) | >18 | >22 | >22 | >21 |
| PHV-101-11 | 0.66(P) | 1.82(P) | 16.7 | >22 | >22 | >21 |
| PHV-101-12 | 3.02(P) | 2.20(P) | 15.5 | >22 | >22 | >21 |
| PHV-101-13 | 2.80(P) | 2.77(P) | >18 | >22 | >22 | >21 |
| PHV-101-14 | 1.91(P) | 0.85(P) | >18 | >22 | >22 | >21 |
| PHV-101-15 | 3.69(P) | 3.24(P) | >18 | >22 | >22 | >21 |

All results are expressed as specimen absorbance to cutoff ratios. Ratios ≧1.0 are considered reactive. The data under "Abbott" and "Ortho" are provided by BBI to customers buying their anti-HCV mixed titer performance panel. The letters P, N and I inside the parentheses stand respectively for "Positive", "Negative" and "Indeterminant"; these data were obtained with the manufacturers' confirmatory EIA or RIBA 2.0 kits and provided by BBI with the panel.

Samples 4, 7 and 19 (Table 3a) are considered anti-HCV negative even though Ortho's EIA gave a low positive signal with sample 19. Samples 8 and 10 were found "indeterminant" by the supplementary Ortho RIBA 2.0 test. These samples were found positive with our synthetic peptides with the exception of sample 10 which tests negative with BCH-437 (SEQ ID NO:6) and BCH-439 (SEQ ID NO:8). In general, it can be seen that the strongest positive signals are obtained with BCH-438 (SEQ ID NO:7) and BCH-439 (SEQ ID NO:8).

This anti-HCV low titer performance panel shown in Table 3b only includes samples which gave signal to cutoff ratios of less than 4.0 using at least one of the two licensed test kits. Sample 2 was found negative by all tests and all synthetic peptides and is thus considered as truly negative. Samples 3 and 5 could not be confirmed positive with the RIBA 2.0 supplementary kit. Peptides BCH-423 (SEQ ID NO:1), BCH-438 (SEQ ID NO:7) and BCH-439 (SEQ ID NO:8) were able to detect these samples as positive. In all other cases, the signal to cutoff ratios measured with the BCH-423 (SEQ ID NO:1), BCH-437 (SEQ ID NO:6), BCH-438 (SEQ ID NO:7) and BCH-439 (SEQ ID NO:8) were much higher than those measured with the two commercially available EIAs.

The results obtained with these two panels of well characterized samples indicate that of the synthetic peptides tested, BCH-423 (SEQ ID NO:1), BCH-438 (SEQ ID NO:7) and BCH-439 (SEQ ID NO:8) are consistently better than the commercially available anti-HCV tests. Our peptides pick up difficult, low-titer samples easily with a high signal to cutoff ratio.

EXPERIMENT 4

The aim of this experiment was to measure the specificity of the four preferred synthetic peptides towards HCV antibodies. To accomplish this, a group of samples (serum and plasma) was collected from 63 normal blood donors. Table 4 summarizes the data obtained when each of these four peptides was tested on this panel of seronegative samples.

TABLE 4

| | EIA WITH SYNTHETIC PEPTIDE | | | |
|---|---|---|---|---|
| | BCH-423 (SEQ ID NO:1) | BCH-437 (SEQ ID NO:6) | BCH-438 (SEQ ID NO:7) | BCH-439 (SEQ ID NO:8) |
| Number of samples tested: | 63 | 63 | 63 | 63 |
| Number of samples found reactive: | 5 | 0 | 0 | 11 |
| Average absorbency value measured on the non-reactive samples: | 0.075 | 0.028 | 0.050 | 0.052 |
| Standard deviation (n) | 0.037(58) | 0.017(63) | 0.040(63) | 0.027(52) |

Table 4 shows that BCH-437 (SEQ ID NO:6) and BCH-438 (SEQ ID NO:7) were 100% accurate, in that neither detected a positive result in any of the 63 seronegative samples. BCH-423 (SEQ ID NO:1) was 92% accurate and BCH-439 (SEQ ID NO:8) was 82% accurate in their assessment of the seronegative samples. Thus, it appears that the amino acid sequence "MSTNP", present on BCH-423 (SEQ ID NO:1) and BCH-439 (SEQ ID NO:8) but absent from BCH-437 (SEQ ID NO:6) and BCH-438 (SEQ ID NO:7), might be responsible for the "false positive" results obtained with BCH-423 (SEQ ID NO:1) and BCH-439 (SEQ ID NO:8).

EXPERIMENT 5

The most preferred peptide of this invention, BCH-438 (SEQ ID NO:7), was tested in association with three other synthetic peptides (BCH-446 (SEQ ID NO:11), BCH-448 (SEQ ID NO:12) and BCH-461 (SEQ ID NO:14)), all of which recognized a majority of the anti-HCV seropositive samples screened in Experiment 1. When tested alone, the concentration of each synthetic peptide was 10 μg/ml. The concentration of BCH-438 in the mixtures was 6.7 μg/ml and the second peptide was present at a concentration of 3.3 μg/ml. Some samples, as indicated, were diluted 50-, 200-, 1000- or 2000-fold using the same sample diluent as before (see Experiment 1 for protocol). Dilution allowed for a more accurate determination of the gain in sensitivity observed with some of the peptide mixtures.

TABLE 5

| | | EIA WITH SYNTHETIC PEPTIDE(S) | | | | | | |
|---|---|---|---|---|---|---|---|---|
| Sample No. | Dilution | BCH-438 (SEQ ID NO:7) | BCH-446 (SEQ ID NO:11) | BCH-448 (SEQ ID NO:12) | BCH-461 (SEQ ID NO:14) | BCH-438 + BCH-446 | BCH-438 + BCH-448 | BCH-438 + BCH-461 |
| 1801-1 | 1/200 | >19 | 18.8 | 19 | 14.7 | >19 | >19 | >19 |
| 1801-2 | 1/200 | >19 | >19 | 16.2 | >19 | >19 | >19 | >19 |
| 1801-3 | 1/50 | 16.6 | 1.3 | 0.3 | 0.7 | 19.4 | 18.5 | 17.3 |
| 1801-12 | 1/200 | >19 | >19 | 4.2 | 0.6 | >19 | >19 | >19 |
| 1801-19 | 1/200 | >19 | >19 | 3.9 | 0.8 | >19 | >19 | >19 |
| 1801-20 | 1/200 | >19 | 12.3 | 3.3 | 3.6 | >19 | >19 | >19 |
| 1801-25 | 1/200 | >19 | >19 | 0.0 | 1.3 | >19 | >19 | >19 |
| 1801-30 | 1/200 | >19 | >19 | 0.1 | 0.1 | >19 | >19 | >19 |
| 1801-31 | 1/200 | >19 | 7.2 | 14.2 | 5.7 | >19 | >19 | >19 |
| 1801-40 | 1/50 | 1.2 | 0.2 | 0.2 | 0.9 | 0.6 | 1.0 | 1.1 |
| 1801-43 | 1/200 | >19 | >19 | >19 | >19 | >19 | >19 | >19 |
| 1801-58 | 1/200 | >19 | >19 | 3.6 | >19 | >19 | >19 | >19 |
| 1801-59 | 1/50 | 2.5 | 0.1 | 0.4 | 0.3 | 1.1 | 2.1 | 2.1 |
| 1801-61 | 1/200 | >19 | >19 | 4.1 | >19 | >19 | >19 | >19 |
| 1801-63 | 1/1000 | >19 | >19 | 0.8 | 14.7 | >19 | >19 | >19 |
| 1801-81 | 1/1000 | 12.2 | 1.7 | 1.2 | 11.0 | 15.7 | 15.0 | 18.0 |
| 1801-82 | 1/1000 | >19 | 10.7 | 17.0 | 9.6 | >19 | >19 | >19 |
| 1801-83 | 1/2000 | >19 | 18.7 | 6.4 | 8.1 | >19 | >19 | >19 |

TABLE 5-continued

| | | EIA WITH SYNTHETIC PEPTIDE(S) | | | | | | |
|---|---|---|---|---|---|---|---|---|
| Sample No. | Dilution | BCH-438 (SEQ ID NO:7) | BCH-446 (SEQ ID NO:11) | BCH-448 (SEQ ID NO:12) | BCH-461 (SEQ ID NO:14) | BCH-438 + BCH-446 | BCH-438 + BCH-448 | BCH-438 + BCH-461 |
| 1801-86 | 1/2000 | 9.8 | 1.4 | 0.9 | 8.2 | 13.0 | 12.2 | 14.8 |
| 1801-90 | 1/2000 | 12.7 | 5.5 | 0.0 | 0.2 | 11.4 | 13.0 | 13.2 |
| 3210-119 | 1/2000 | 11.9 | 3.0 | 0.1 | 0.3 | 14.3 | 11.9 | 11.8 |
| 3210-127 | 1/2000 | 7.6 | 18.8 | 0.0 | 0.1 | 18.3 | 8.2 | 8.1 |
| PHV-101-03 | 1/50 | 1.7 | 0.8 | 0.4 | 0.7 | 2.0 | 1.7 | 1.8 |
| PHV-101-05 | 1/50 | 2.2 | 1.1 | 0.5 | 1.1 | 2.9 | 3.3 | 2.9 |
| PHV-201-10 | 1/50 | 2.3 | 0.4 | 0.1 | 0.2 | 0.9 | 1.6 | 1.5 |
| PHV-201-20 | 1/50 | 2.6 | .05 | 0.4 | 4.7 | 2.5 | 2.9 | 5.6 |

Table 5 shows that mixtures of BCH-438 (SEQ ID NO:7) in association with BCH-446 (SEQ ID NO:11), BCH-448 (SEQ ID NO:12) or BCH-461 (SEQ ID NO:14) detect an equal or higher signal to cutoff ratio for 81%, 88% and 85%, respectively, of the seropositive samples tested as compared to the ratio obtained using BCH-438 (SEQ ID NO:7) alone. The increase in sensitivity observed with the BCH-438 (SEQ ID NO:7)/BCH-461 (SEQ ID NO:14) mixture is especially noteworthy. Several samples found to be low-positive with BCH-438 (SEQ ID NO:7) alone (e.g., 1801-81, 1801-86 and PHV-201-20) have significantly augmented signals when tested with the BCH-438 (SEQ ID NO:7)/BCH-461 (SEQ ID NO:14) mixture.

While we have herein before presented a number of embodiments of this invention, it is apparent that our basic construction can be altered to provide other embodiments which utilize the processes and compositions of this invention. Therefore, it will be appreciated that the scope of this invention is defined by the claims appended hereto rather than by the specific embodiments which have been presented hereinabove by way of example.

We claim:

1. A mixture comprising two or more peptides having the formula a — X — c — Z — b wherein:

X and Z are independently selected from the group of amino acid sequences consisting of:

| (SEQ ID NO:1) | -MSTNPKPQRKTKRNTNRRPQDVKFPG- | (BCH-423) |
|---|---|---|
| (SEQ ID NO:5) | -PQDVKFPGGGQIV- | (BCH-436) |
| (SEQ ID NO:6) | -KRNTNRRPQDVKFPGGGQIV- | (BCH-437) |
| (SEQ ID NO:7) | -KPQRKTKRNTNRRPQDVKFPGGGQIV- | (BCH-438) |

-continued

| (SEQ ID NO:8) | -MSTNPKPQRKTKRNTNRRPQDVKFPGGGQIV- | (BCH-439) |
|---|---|---|
| (SEQ ID NO:10) | -RGSRPSWGPNDPRRRSRNLGKVIDTLT- | (BCH-443) |
| (SEQ ID NO:11) | -KFPGGGQIVGGVYLLPRRGPRLGV- | (BCH-446) |
| (SEQ ID NO:12) | -RGRRQPIPKARRPEGRTWAQPGY- | (BCH-448) |
| (SEQ ID NO:14) | -GPRLGVRATRKTSERSQPRGRRQPI- | (BCH-461) |
| (SEQ ID NO:13) | -SSIVYEAADVIMHAPGSVPSVR- | (BCH-458) | and wherein:

a is an amino acid terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide; and c is a linker of one or two amino acids or a substituent effective to facilitate coupling of the two peptides in tandem or to improve the immunogenic or antigenic activity of the tandem peptide.

2. A peptide having the formula a — X — c — Z — b wherein:

X and Z are independently selected from the group of amino acid sequences consisting of:

| (SEQ ID NO:1) | -MSTNPKPQRKTKRNTNRRPQDVKFPG- | (BCH-423) |
|---|---|---|
| (SEQ ID NO:5) | -PQDVKFPGGGQIV- | (BCH-436) |
| (SEQ ID NO:6) | -KRNTNRRPQDVKFPGGGQIV- | (BCH-437) |
| (SEQ ID NO:7) | -KPQRKTKRNTNRRPQDVKFPGGGQIV- | (BCH-438) |
| (SEQ ID NO:8) | -MSTNPKPQRKTKRNTNRRPQDVKFPGGGQIV- | (BCH-439) |
| (SEQ ID NO:10) | -RGSRPSWGPNDPRRRSRNLGKVIDTLT- | (BCH-443) |
| (SEQ ID NO:11) | -KFPGGGQIVGGVYLLPRRGPRLGV- | (BCH-446) |
| (SEQ ID NO:12) | -RGRRQPIPKARRPEGRTWAQPGY- | (BCH-448) |
| (SEQ ID NO:14) | -GPRLGVRATRKTSERSQPRGRRQPI- | (BCH-461) |
| (SEQ ID NO:13) | -SSIVYEAADVIMHAPGSVPSVR- | (BCH-458) | and wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide; and c is a linker of one or two amino acids or a substituent effective to facilitate coupling of the two peptides in tandem or to improve the immunogenic or antigenic activity of the tandem peptide.

3. A mixture comprising two or more of the following peptides:

| | | |
|---|---|---|
| (SEQ ID NO:1) | a-MSTNPKPQRKTKRNTNRRPQDVKFPG-b | (BCH-423) |
| (SEQ ID NO:5) | a-PQDVKFPGGGQIV-b | (BCH-436) |
| (SEQ ID NO:6) | a-KRNTNRRPQDVKFPGGGQIV-b | (BCH-437) |
| (SEQ ID NO:7) | a-KPQRKTKRNTNRRPQDVKFPGGGQIV-b | (BCH-438) |
| (SEQ ID NO:8) | a-MSTNPKPQRKTKRNTNRRPQDVKFPGGGQIV-b | (BCH-439) |
| (SEQ ID NO:10) | a-RGSRPSWGPNDPRRRSRNLGKVIDTLT-b | (BCH-443) |
| (SEQ ID NO:11) | a-KFPGGGQIVGGVYLLPRRGPRLGV-b | (BCH-446) |
| (SEQ ID NO:12) | a-RGRRQPIPKARRPEGRTWAQPGY-b | (BCH-448) |
| (SEQ ID NO:14) | a-GPRLGVRATRKTSERSQPRGRRQPI-b | (BCH-461) |
| (SEQ ID NO:13) | a-SSIVYEAADVIMHAPGSVPSVR-b | (BCH-458) | wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide.

4. A peptide selected from the group consisting of:

| | | |
|---|---|---|
| (SEQ ID NO:7) | a-KPQRKTKRNTNRRPQDVKFPGGGQIV-b | (BCH-438) |
| and | | |
| (SEQ ID NO:14) | a-GPRLGVRATRKTSERSQPRGRRQPI-b | (BCH-461) | wherein:

| | | |
|---|---|---|
| (SEQ ID NO:1) | a-MSTNPKPQRKTKRNTNRRPQDVKFPG-b | (BCH-423) |
| (SEQ ID NO:5) | a-PQDVKFPGGGQIV-b | (BCH-436) |
| (SEQ ID NO:6) | a-KRNTNRRPQDVKFPGGGQIV-b | (BCH-437) |
| (SEQ ID NO:7) | a-KPQRKTKRNTNRRPQDVKFPGGGQIV-b | (BCH-438) |
| (SEQ ID NO:8) | a-MSTNPKPQRKTKRNTNRRPQDVKFPGGGQIV-b | (BCH-439) |
| (SEQ ID NO:10) | a-RGSRPSWGPNDPRRRSRNLGKVIDTLT-b | (BCH-443) |
| (SEQ ID NO:11) | a-KFPGGGQIVGGVYLLPRRGPRLGV-b | (BCH-446) |
| (SEQ ID NO:12) | a-RGRRQPIPKARRPEGRTWAQPGY-b | (BCH-448) |
| (SEQ ID NO:14) | a-GPRLGVRATRKTSERSQPRGRRQPI-b | (BCH-461) |
| (SEQ ID NO:13) | a-SSIVYEAADVIMHAPGSVPSVR-b | (BCH-458) | wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide.

5. A peptide selected from the group consisting of:

| | | |
|---|---|---|
| (SEQ ID NO:1) | a-MSTNPKPQRKTKRNTNRRPQDVKFPG-b | (BCH-423) |
| (SEQ ID NO:6) | a-KRNTNRRPQDVKFPGGGQIV-b | (BCH-437) |
| (SEQ ID NO:7) | a-KPQRKTKRNTNRRPQDVKFPGGGQIV-b | (BCH-438) |
| (SEQ ID NO:8) | a-MSTNPKPQRKTKRNTNRRPQDVKFPGGGQIV-b | (BCH-439) | wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide.

6. A mixture comprising peptides of the formula:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide.

7. A peptide having the formula:

a-KPQRKTKRNTNRRPQDVKFPGGGQIV-b        (BCH-438)

wherein:

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Ser  Thr  Asn  Pro  Lys  Pro  Gln  Arg  Lys  Thr  Lys  Arg  Asn  Thr  Asn
1                 5                           10                          15
Arg  Arg  Pro  Gln  Asp  Val  Lys  Phe  Pro  Gly
                 20                      25
```

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala  Tyr  Glu  Val  Arg  Asn  Val  Ser  Gly  Ile  Tyr  His  Val  Thr  Asn  Asp
1                 5                           10                          15
Ser  Ser
```

( 2 ) INFORMATION FOR SEQ ID NO:3:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

```
His Ala Pro Gly Ser Val Pro Ser Val Arg Glu Asn Asn Ser Ser Arg
 1               5                  10                  15
Cys Trp Val Ala Leu Thr
             20
```

( 2 ) INFORMATION FOR SEQ ID NO:4:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Gly Ser Val Phe Leu Ile Ser Gln Leu Phe Thr Phe Ser Pro Arg Arg
 1               5                  10                  15
His Glu Thr Val Gln Asp
             20
```

( 2 ) INFORMATION FOR SEQ ID NO:5:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

```
Pro Gln Asp Val Lys Phe Pro Gly Gly Gly Gln Ile Val
 1               5                  10
```

( 2 ) INFORMATION FOR SEQ ID NO:6:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

```
Lys Arg Asn Thr Asn Arg Arg Pro Gln Asp Val Lys Phe Pro Gly Gly
 1               5                  10                  15
Gly Gln Ile Val
             20
```

( 2 ) INFORMATION FOR SEQ ID NO:7:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Lys Pro Gln Arg Lys Thr Lys Arg Asn Thr Asn Arg Arg Pro Gln Asp
  1               5                      10                      15
Val Lys Phe Pro Gly Gly Gly Gln Ile Val
                20              25
```

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Met Ser Thr Asn Pro Lys Pro Gln Arg Lys Thr Lys Arg Asn Thr Asn
  1               5                      10                      15
Arg Arg Pro Gln Asp Val Lys Phe Pro Gly Gly Gly Gln Ile Val
                20              25                      30
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Thr Thr Leu Arg Arg His Val Asp Leu Leu Val Gly Thr Ala Ala Phe
  1               5                      10                      15
Cys Ser Ala Met Tyr Val Gly Asp Leu Cys Gly Ser Val
                20              25
```

( 2 ) INFORMATION FOR SEQ ID NO:10:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Arg Gly Ser Arg Pro Ser Trp Gly Pro Asn Asp Pro Arg Arg Arg Ser
  1               5                      10                      15
Arg Asn Leu Gly Lys Val Ile Asp Thr Leu Thr
                20              25
```

( 2 ) INFORMATION FOR SEQ ID NO:11:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
    Lys  Phe  Pro  Gly  Gly  Gly  Gln  Ile  Val  Gly  Gly  Val  Tyr  Leu  Leu  Pro
    1              5                        10                       15

Arg  Arg  Gly  Pro  Arg  Leu  Gly  Val
                   20
```

( 2 ) INFORMATION FOR SEQ ID NO:12:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:12:

```
    Arg  Gly  Arg  Arg  Gln  Pro  Ile  Pro  Lys  Ala  Arg  Arg  Pro  Glu  Gly  Arg
    1              5                        10                       15

Thr  Trp  Ala  Gln  Pro  Gly  Tyr
                   20
```

( 2 ) INFORMATION FOR SEQ ID NO:13:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

```
    Ser  Ser  Ile  Val  Tyr  Glu  Ala  Ala  Asp  Val  Ile  Met  His  Ala  Pro  Gly
    1              5                        10                       15

Ser  Val  Pro  Ser  Val  Arg
                   20
```

( 2 ) INFORMATION FOR SEQ ID NO:14:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:14:

```
    Gly  Pro  Arg  Leu  Gly  Val  Arg  Ala  Thr  Arg  Lys  Thr  Ser  Glu  Arg  Ser
    1              5                        10                       15

Gln  Pro  Arg  Gly  Arg  Arg  Gln  Pro  Ile
                   20                      25
```

( 2 ) INFORMATION FOR SEQ ID NO:15:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

```
    Thr  Ala  Ala  Leu  Val  Val  Ser  Gln  Leu  Leu  Arg  Ile  Pro  Gln  Ala  Val
    1              5                        10                       15

Met  Asp  Met  Val  Ala  Gly  Ala
```

( 2 ) INFORMATION FOR SEQ ID NO:16:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Met Ser Thr Asn Pro Lys Pro Gln Arg Lys Thr Lys Arg Asn Thr Asn
 1               5                  10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
            35                  40                  45
Thr Arg Lys Thr Ser Glu Arg Ser Gln Pro Arg Gly Arg Arg Gln Pro
        50                  55                  60
Ile Pro Lys Ala Arg Arg Pro Glu Gly Arg Thr Trp Ala Gln Pro Gly
 65                 70                  75                  80
Tyr Pro Trp Pro Leu Tyr Gly Asn Glu Gly Leu Gly Trp Ala Gly Trp
                85                  90                  95
Leu Leu Ser Pro Arg Gly Ser Arg Pro Ser Trp Gly Pro Asn Asp Pro
           100                 105                 110
Arg Arg Arg Ser Arg Asn Leu Gly Lys Val Ile Asp Thr Leu Thr Cys
           115                 120                 125
Gly Phe Ala Asp Leu Met Gly Tyr Ile Pro Leu Val Gly Ala Pro Leu
       130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Ile Pro Ala Ser
            180                 185                 190
```

( 2 ) INFORMATION FOR SEQ ID NO:17:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Ala Tyr Glu Val Arg Asn Val Ser Gly Ile Tyr His Val Thr Asn Asp
 1               5                  10                  15
Cys Ser Asn Ser Ser Ile Val Tyr Glu Ala Ala Asp Val Ile Met His
            20                  25                  30
Ala Pro Gly Cys Val Pro Cys Val Arg Glu Asn Asn Ser Ser Arg Cys
            35                  40                  45
Trp Val Ala Leu Thr Pro Thr Leu Ala Ala Arg Asn Ala Ser Val Pro
        50                  55                  60
Thr Thr Thr Leu Arg Arg His Val Asp Leu Leu Val Gly Thr Ala Ala
 65                 70                  75                  80
Phe Cys Ser Ala Met Tyr Val Gly Asp Leu Cys Gly Ser Val Phe Leu
```

| | | | | | | | | | | | | | | |
|---|---|---|---|---|---|---|---|---|---|---|---|---|---|---|
| | | | | 85 | | | | 90 | | | | | 95 | |
| Ile | Ser | Gln | Leu 100 | Phe | Thr | Phe | Ser | Pro 105 | Arg | Arg | His | Glu | Thr 110 | Val | Gln |
| Asp | Cys | Asn 115 | Cys | Ser | Ile | Tyr | Pro 120 | Gly | His | Val | Ser | Gly 125 | His | Arg | Met |
| Ala | Trp 130 | Asp | Met | Met | Met | Asn 135 | Trp | Ser | Pro | Thr | Ala 140 | Ala | Leu | Val | Val |
| Ser 145 | Gln | Leu | Leu | Arg | Ile 150 | Pro | Gln | Ala | Val | Met 155 | Asp | Met | Val | Ala | Gly 160 |
| Ala | His | Trp | Gly | Val 165 | Leu | Ala | Gly | Leu | Ala 170 | Tyr | Tyr | Ser | Met | Val 175 | Gly |
| Asn | Trp | Ala | Lys 180 | Val | Leu | Ile | Val | Met 185 | Leu | Leu | Phe | Ala | Gly 190 | | |